US012708419B2

(12) United States Patent
Niver

(10) Patent No.: US 12,708,419 B2
(45) Date of Patent: Aug. 18, 2026

(54) ORTHOPEDIC COMPRESSION DEVICE

(71) Applicant: Medline Industries, LP, Northfield, IL (US)

(72) Inventor: Ryan Niver, Glenview, IL (US)

(73) Assignee: Medline Industries, LP, Northfield, IL (US)

( * ) Notice: Subject to any disclaimer, the term of this patent is extended or adjusted under 35 U.S.C. 154(b) by 125 days.

(21) Appl. No.: 18/527,644

(22) Filed: Dec. 4, 2023

(65) Prior Publication Data

US 2025/0177022 A1 Jun. 5, 2025

(51) Int. Cl.

| | |
|---|---|
| ***A61B 17/86*** | (2006.01) |
| ***A61B 17/84*** | (2006.01) |
| *A61B 17/00* | (2006.01) |
| *A61B 17/56* | (2006.01) |
| *A61B 17/68* | (2006.01) |

(52) U.S. Cl.

CPC ........ *A61B 17/8685* (2013.01); *A61B 17/842* (2013.01); *A61B 17/844* (2013.01); *A61B 17/8605* (2013.01); *A61B 17/863* (2013.01); *A61B 2017/00526* (2013.01); *A61B 2017/00867* (2013.01); *A61B 2017/564* (2013.01); *A61B 2017/681* (2013.01)

(58) Field of Classification Search

CPC . A61B 17/8685; A61B 17/844; A61B 17/842; A61B 17/7225; A61B 17/7216; A61B 17/8014; A61B 2017/681

See application file for complete search history.

(56) References Cited

U.S. PATENT DOCUMENTS

| | | | |
|---|---|---|---|
| 11,224,467 | B2 | 1/2022 | Peterson |
| 11,234,746 | B2 | 2/2022 | Peterson |
| 11,291,488 | B1 | 4/2022 | O'Flaherty |
| 11,317,956 | B1 | 5/2022 | Gregersen |
| 11,744,625 | B2 | 9/2023 | O'Flaherty |
| 11,998,255 | B1 | 6/2024 | Gregersen |
| 12,023,068 | B2 | 7/2024 | Blair |
| 12,569,285 | B2 | 3/2026 | O'Flaherty |

(Continued)

FOREIGN PATENT DOCUMENTS

| | | |
|---|---|---|
| WO | 2017147537 | 8/2017 |

*Primary Examiner* — Amy R Sipp
(74) *Attorney, Agent, or Firm* — Fitch, Even, Tabin & Flannery LLP

(57) ABSTRACT

An orthopedic compression device comprises an outer shaft portion having a threaded outer distal end and having an inner cannulation extending from an opening in a proximal end towards an inner distal end, the inner cannulation having a proximal region; a head portion, the head portion having a distal end portion with a geometry keyed to the proximal region of the cannulation of the first shaft to allow rotation of the head portion to drive rotation of the outer shaft portion, the head portion including an inner channel; and an inner shaft portion. The inner shaft portion is formed from a superelastic material and has a stop at a proximal end thereof. The stop engages a stop surface formed within the head portion when the inner shaft portion extends through the inner channel. The inner shaft portion is coupled to the outer shaft portion such that the inner shaft portion elongates and is placed into tension upon separation of the head portion and outer shaft portion.

12 Claims, 14 Drawing Sheets

(56) References Cited

U.S. PATENT DOCUMENTS

2006/0264954 A1* 11/2006 Sweeney, II ....... A61B 17/8685 606/328
2009/0264885 A1* 10/2009 Grant ................... A61B 17/746 606/65
2010/0036440 A1* 2/2010 Morris ................... A61B 17/72 606/320
2010/0076498 A1* 3/2010 Tyber .................... A61F 2/4003 606/302

* cited by examiner

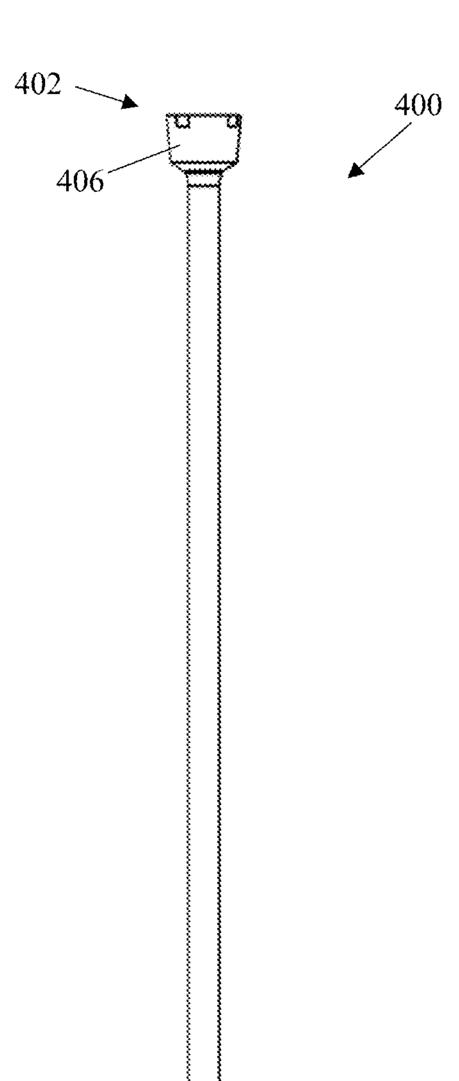
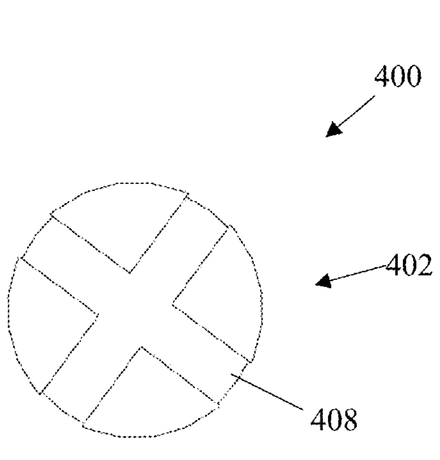
FIG. 15
FIG. 14
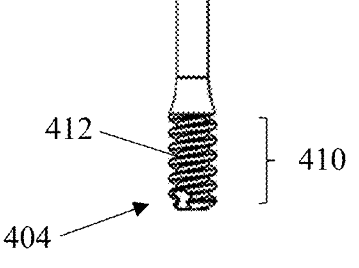

ORTHOPEDIC COMPRESSION DEVICE

FIELD

The disclosure relates to medical instruments and, more particularly, to an implement, kit, and method for providing continuous compression to a fracture.

BACKGROUND

Surgical procedures such as fracture repairs, fusions, or osteotomies require bone tissue to form between bone segments. The ability for successful bone tissue growth at the site of the bone segments is improved when the bone segments are under compression. If there is no compression, a gap may form between the bone segments or healing may otherwise be inhibited. One method to achieve compression is the use of compression screws and similar compression devices. It is desired to provide an orthopedic compression device that may be placed across a bone interface to cause a compressive force across the bone interface.

The disclosure now provides an orthopedic compression device that comprises an outer shaft portion, an inner shaft portion, and a head portion. The outer shaft portion has a threaded outer distal end and an inner cannulation extending from an opening in the proximal end towards an inner distal end, the inner cannulation having a proximal region. The head portion has a distal end portion with a geometry keyed to the proximal region of the cannulation of the first shaft to allow rotation of the head portion to drive rotation of the outer shaft portion. The head portion includes an inner channel. The inner shaft portion is formed from a superelastic material and has a stop at a proximal end thereof. The stop engages a stop surface formed within the head portion when the inner shaft portion extends through the inner channel. The inner shaft portion is coupled to the outer shaft portion such that the inner shaft portion elongates and is placed into tension upon separation of the head portion and outer shaft portion. When placed across a bone interface and when the device is driven into bone sufficiently to cause separation of the head portion and outer shaft portion, the device elongates and the inner shaft portion is placed into tension via its superelastic property, thus causing a compressive force across the bone interface.

Also disclosed are a kit with the above-described orthopedic compression device and a driver, a method of assembling the orthopedic compression device, and a method of using the orthopedic compression device.

BRIEF DESCRIPTION OF THE DRAWINGS

FIG. 14 is front elevation view of the inner shaft portion of the orthopedic compression device of FIG. 1;

FIG. 15 is a top plan view of the inner shaft portion shown in FIG. 14;

Figure 1:
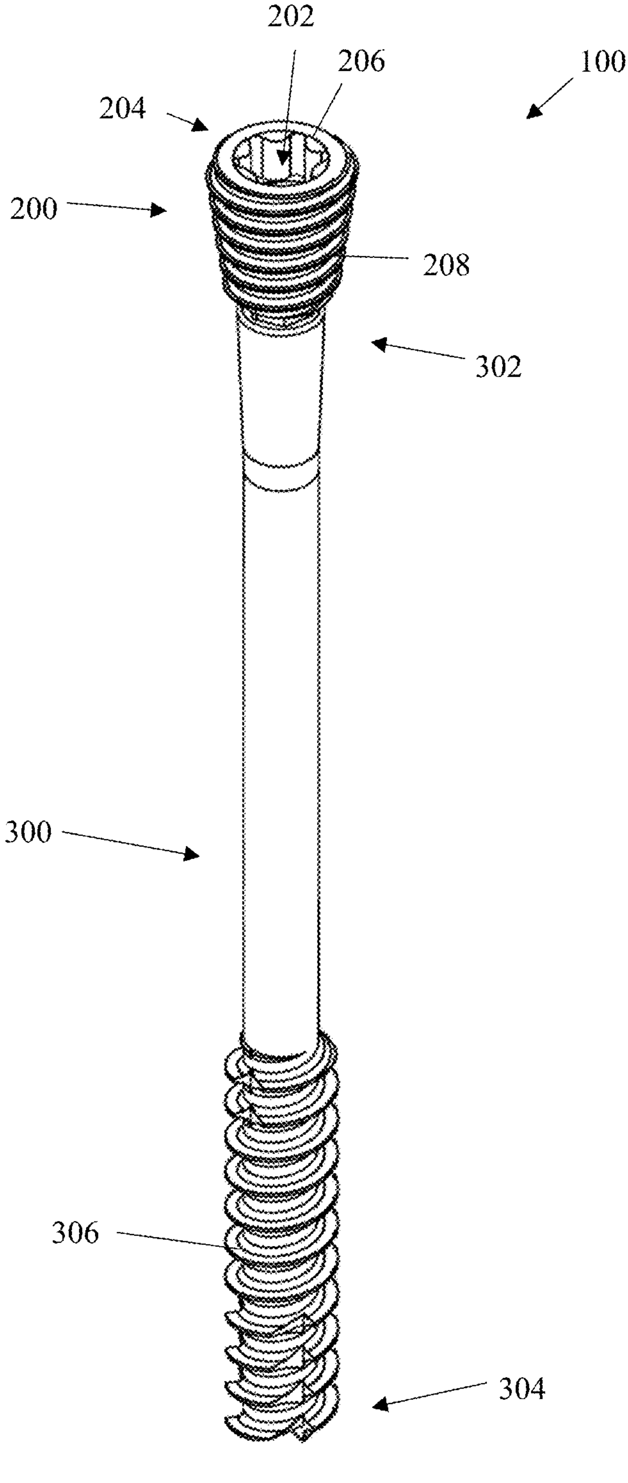
FIG. 1 is an isometric view of an orthopedic compression device in accordance with the present disclosure, shown with the inner shaft in a tensioned position.
Figure 2:
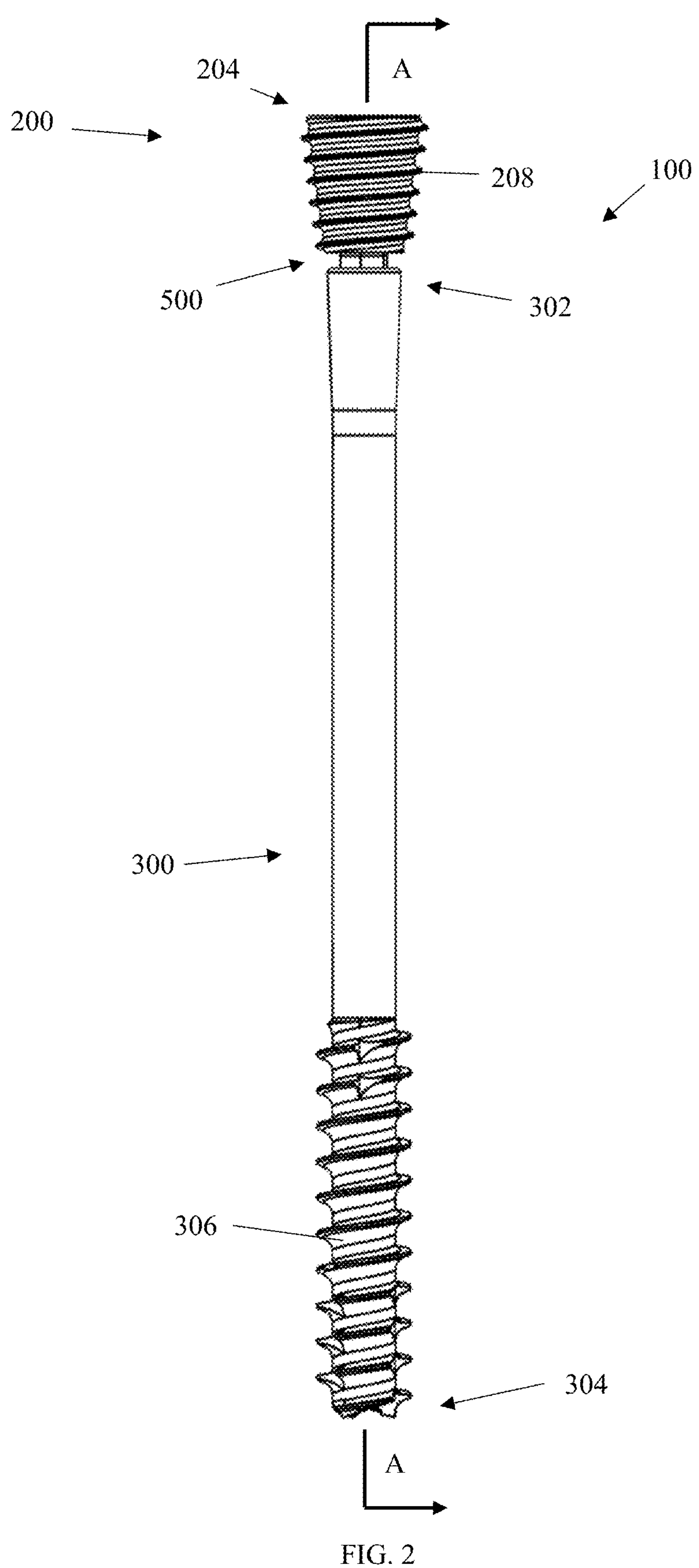
FIG. 2 is a front elevation view of the orthopedic compression device of FIG. 1.
Figure 3:
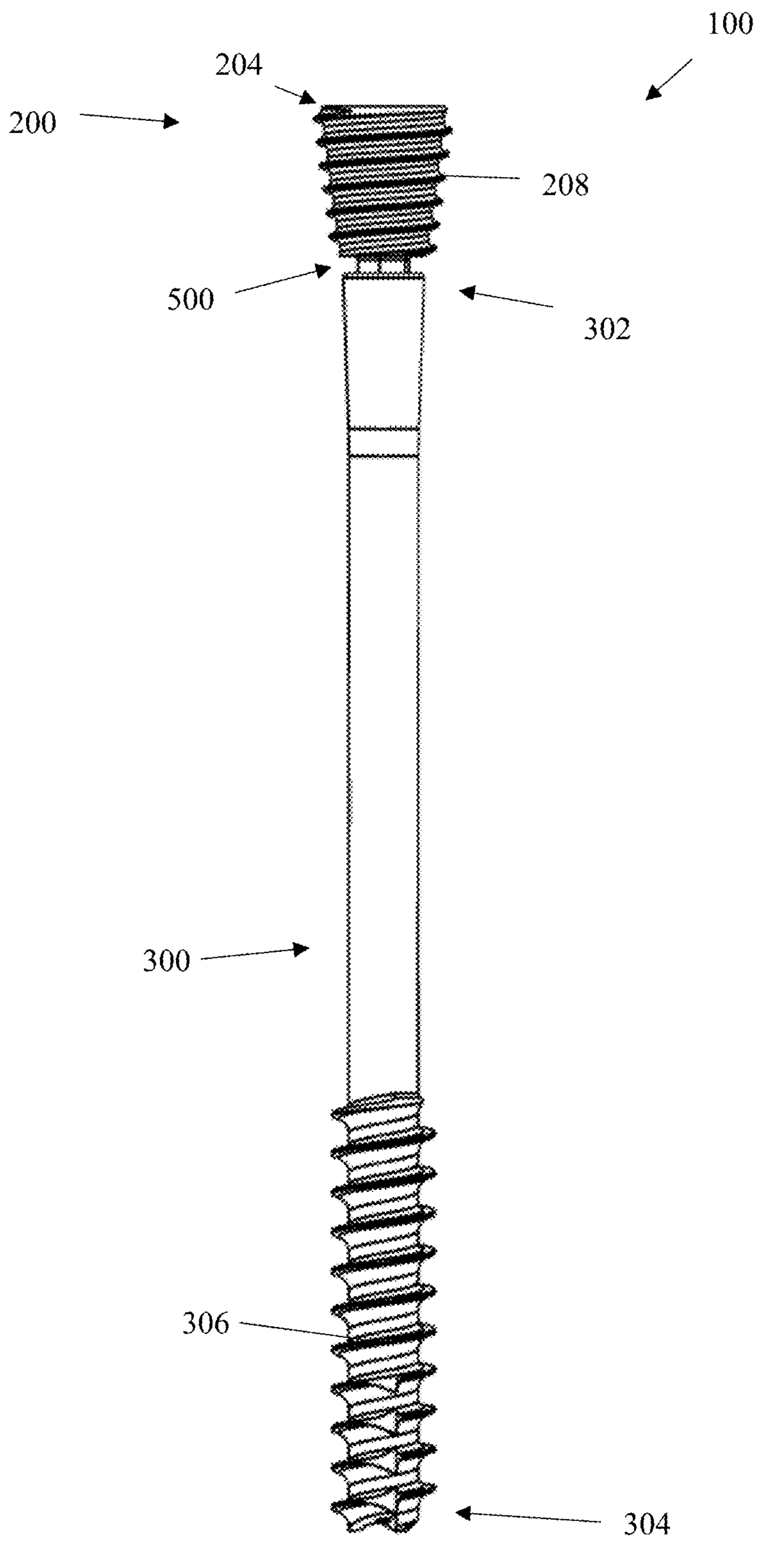
FIG. 3 is a rear elevation view of the orthopedic compression device of FIG. 1.
Figure 4:
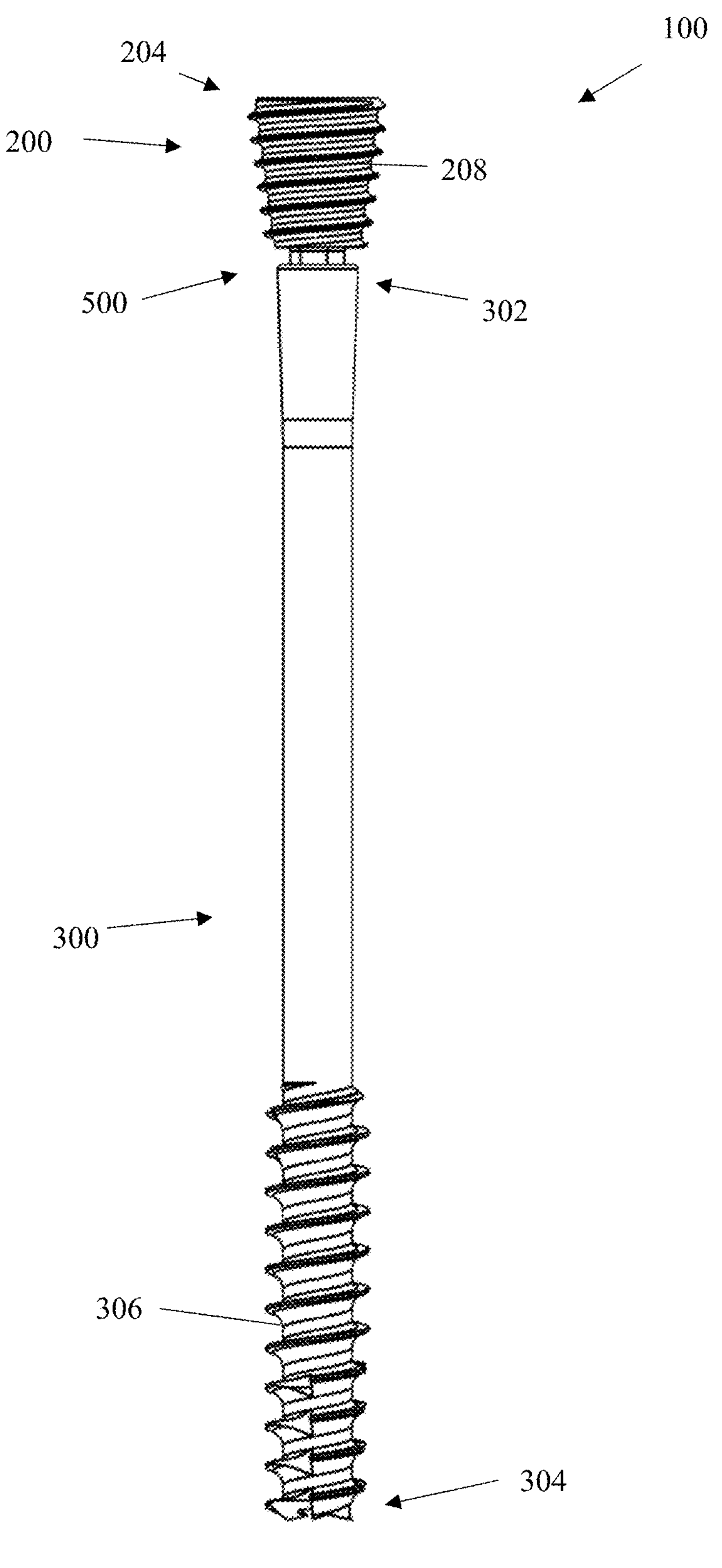
FIG. 4 is a right side elevation view of the orthopedic compression device of FIG. 1.
Figure 5:
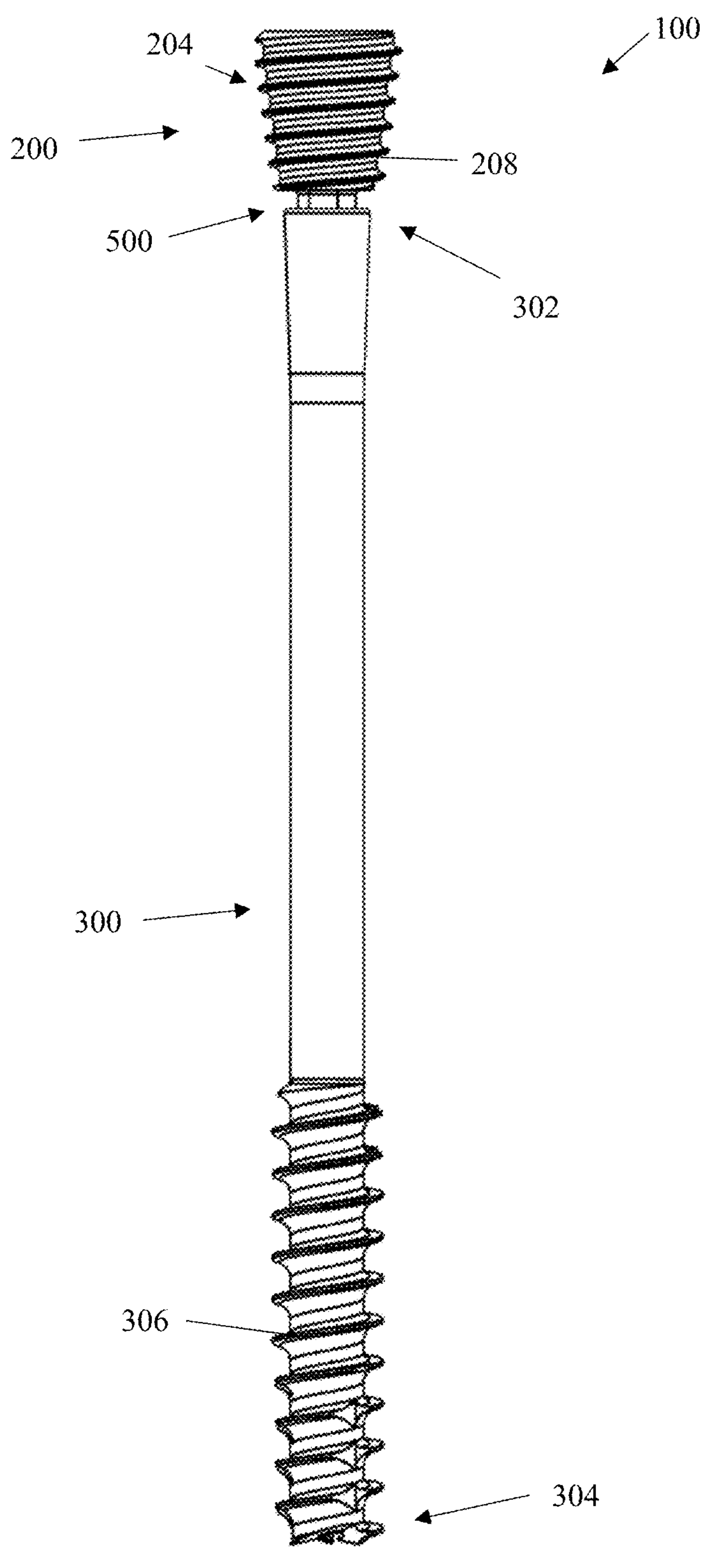
FIG. 5 is a left side elevation view of the orthopedic compression device of FIG. 1.
Figure 6:
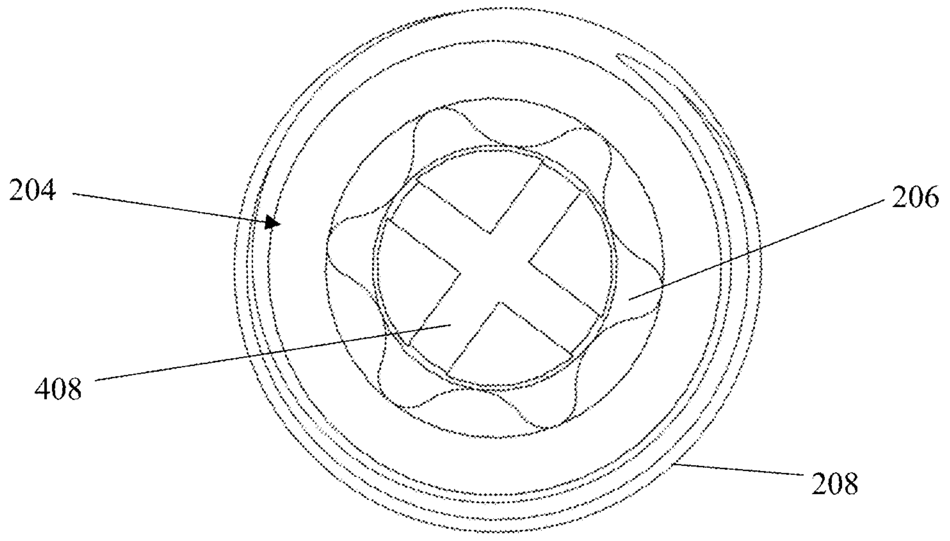
FIG. 6 is a top plan view of the orthopedic compression device of FIG. 1.
Figure 7:
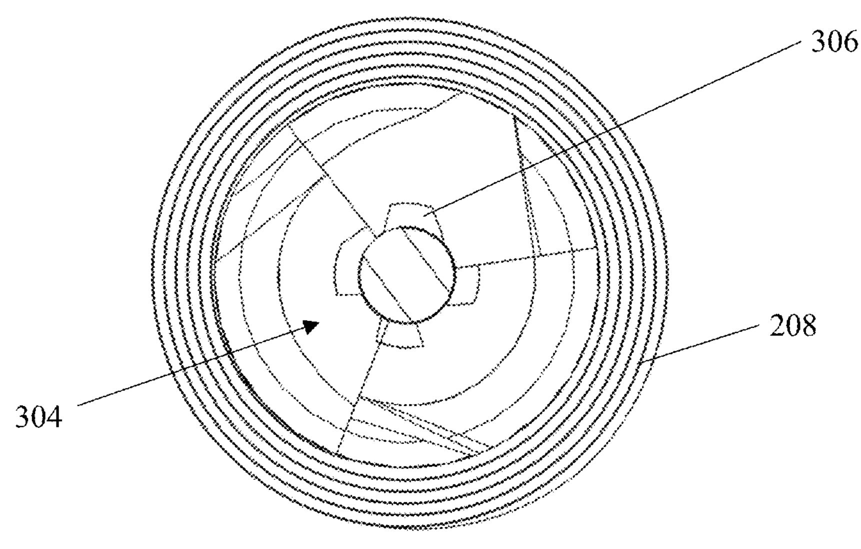
FIG. 7 is a bottom plan view of the orthopedic compression device of FIG. 1.

Terms of orientation are for convenient reference to the Figures and in particular the orientation of the orthopedic compression device in FIG. 1. In practice, the device is omnidirectional and may be oriented in other positions.

DETAILED DESCRIPTION

Figure 8:
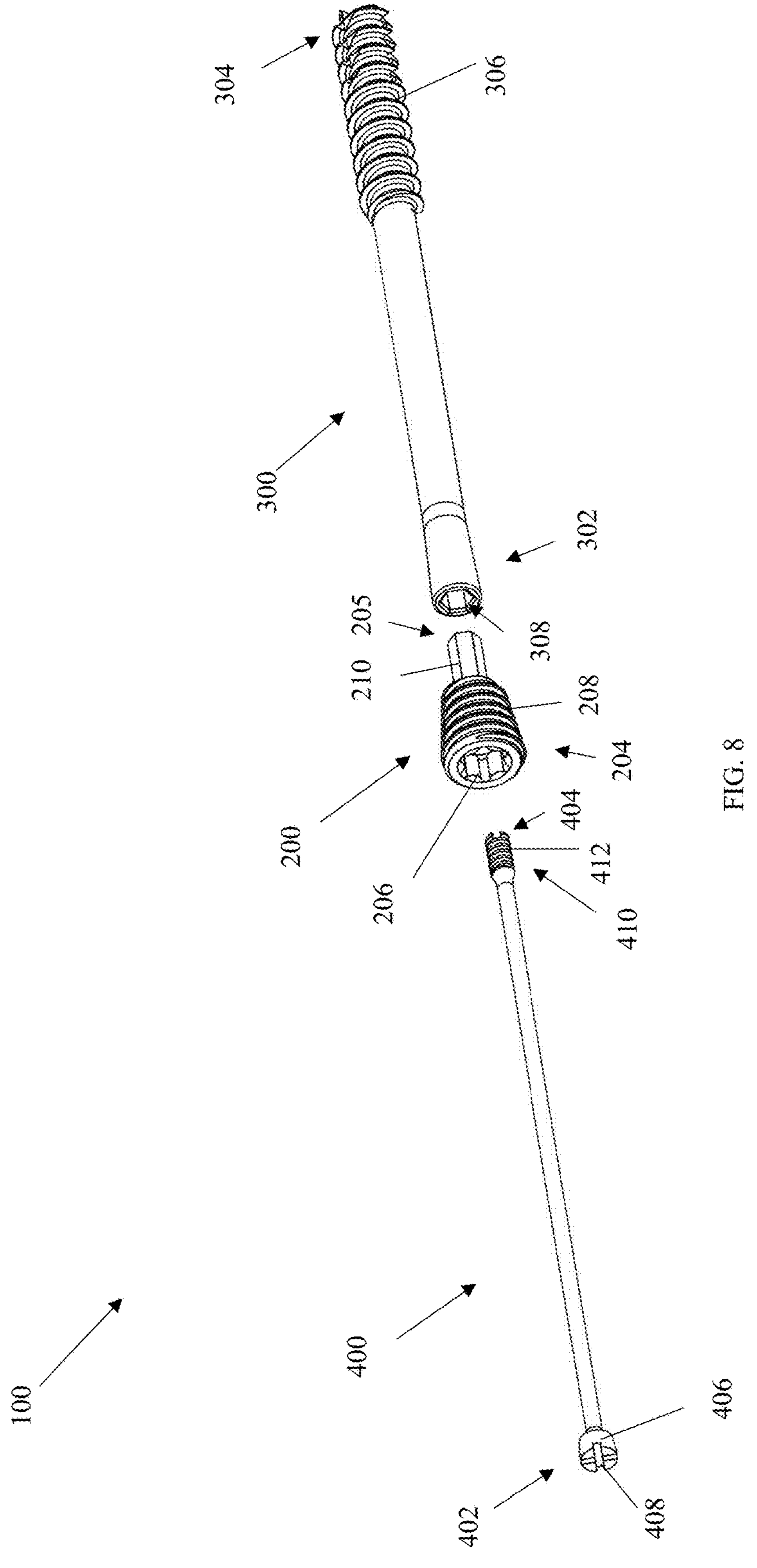
FIG. 8 is an exploded view of the orthopedic compression device of FIG. 1.
Figure 9:
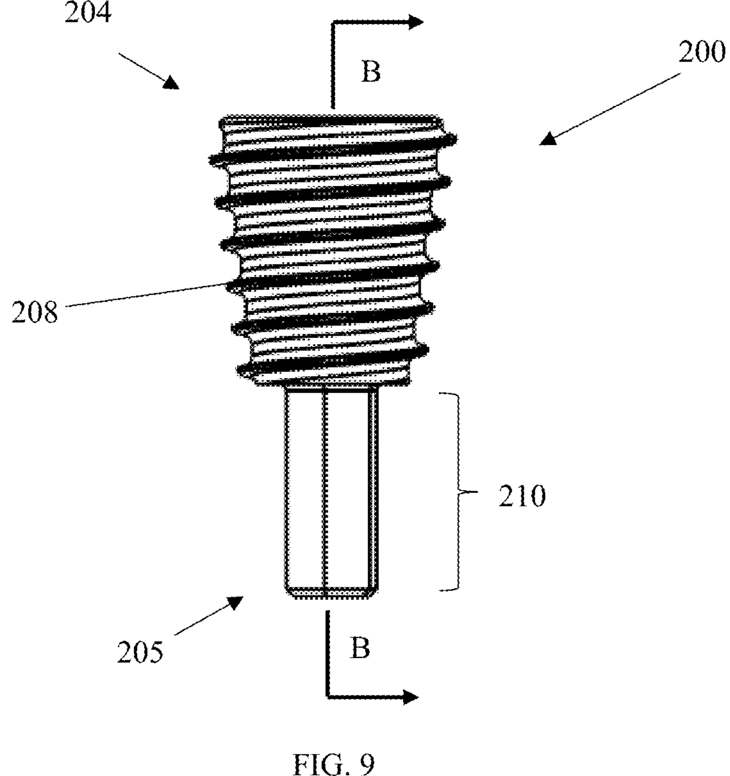
FIG. 9 is front elevation view of a head portion of the orthopedic compression device of FIG. 1.

With reference to FIGS. 1-8, the orthopedic compression device 100 includes a head portion 200 and an outer shaft portion 300. The head portion 200 includes an inner channel 202 formed therein between a proximal end 204 and a distal end 205 (FIG. 8). The head portion 200 also includes a first driver interface 206 configured to receive a corresponding first driver 700 (FIG. 18) to be used to secure the orthopedic compression device 100 within a patient as described further herein below. As shown, the first driver interface 206 is a star driver slot such as a TORX driver slot. The head portion 200 of this embodiment also includes a thread 208 disposed on an external surface of the head portion 200, it being understood that the head portion might be provided without a threaded external surface in other embodiments. The thread 208 is configured to engage bone to secure the head portion 200 within a patient. The outer shaft portion 300 includes a proximal end 302, an inner distal end 304, and a thread 306 disposed on an external surface of the outer shaft portion 300 proximate to the inner distal end 304. The thread 306 is configured to engage bone to secure the inner distal end 304 of the outer shaft portion 300 within the patient. In some embodiments, the thread 306 and the thread 208 can have different pitches to aid in compression of bone segments as the orthopedic compression device 100 is advanced into a patient. This is seen for example in FIG. 2, wherein threading on the head portion 200 has a different thread pitch from the pitch of threading on the outer distal end of the outer shaft portion 300.

With reference to FIG. 8, the orthopedic compression device 100 also includes an inner shaft portion 400. The inner shaft portion 400 is formed from a superelastic material, preferably a nitinol alloy or similar superelastic material. The inner shaft portion 400 includes a proximal end 402 and a distal end 404. The inner shaft portion 400 has a stop 406 monolithically formed at the proximal end 402, a second driver interface 408 on the proximal end 402, and a distal end portion 410 with a thread 412 disposed thereon. The second driver interface 408 is different from the first driver interface 206 and is configured to receive a corresponding second driver 750 (FIG. 18) used to secure the inner shaft portion 400 within the outer shaft portion 300 during assembly. In particular, the inner shaft portion 400 is coupled to an inside of an inner cannulation 308 of the outer shaft portion 300. The inner cannulation 308 extends from an opening in the proximal end 302 to the inner distal end 304 of the outer shaft portion 300. As shown, the second driver interface 408 includes a Phillips driver slot as shown in FIG. 15. Different driver interfaces may be employed.

Figure 10:
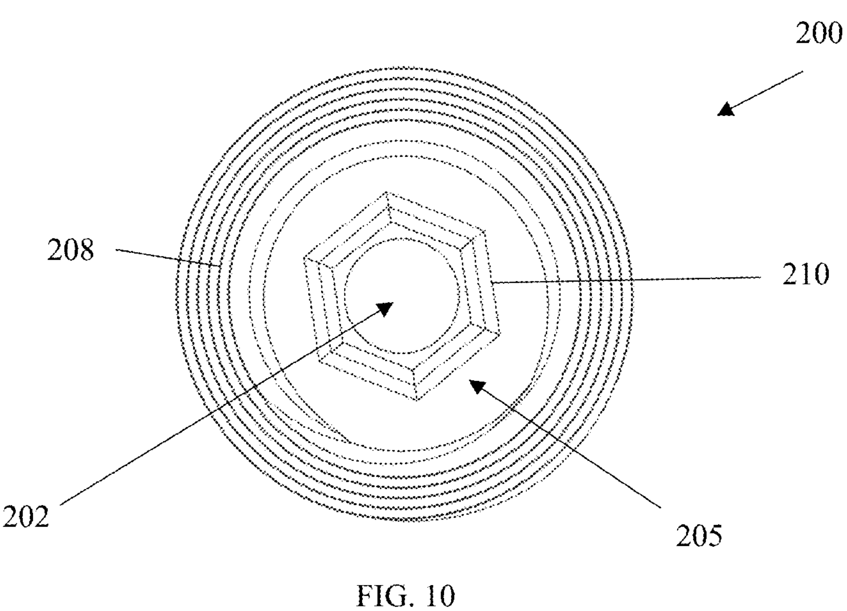
FIG. 10 is bottom plan view of the head portion of FIG. 9.
Figure 11:
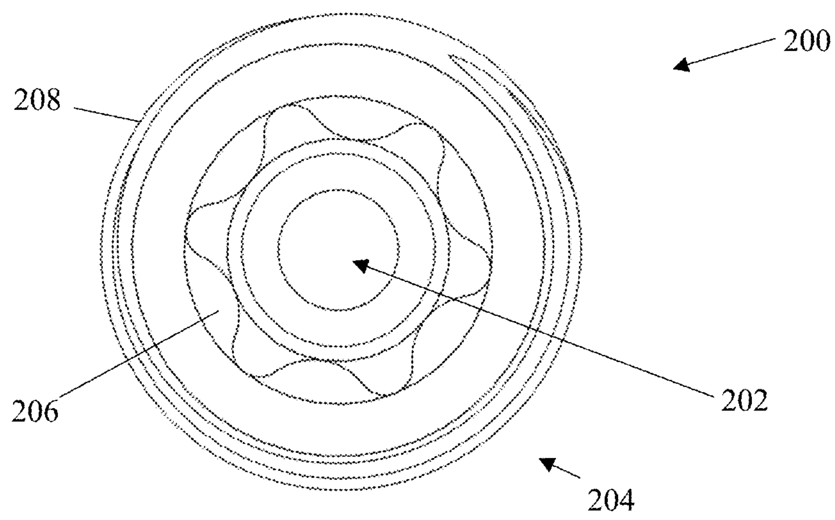
FIG. 11 is top plan view of the head portion of FIG. 9.
Figure 12:
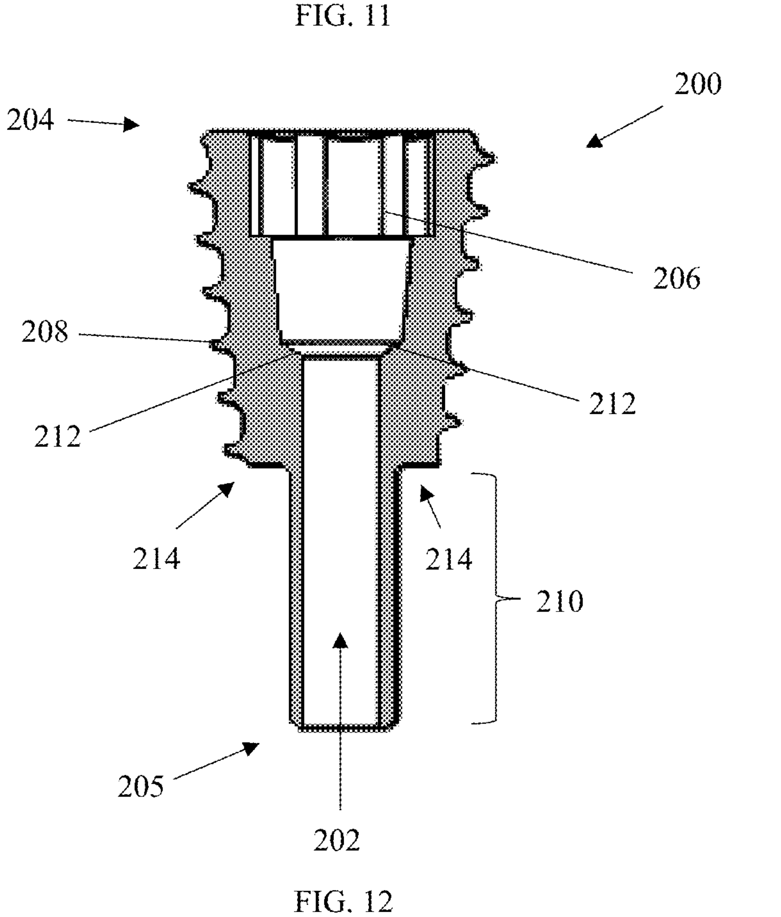
FIG. 12 is cross-sectional view of the head portion of FIG. 9 taken along line B-B in FIG. 9.

With reference now to FIGS. 8-13, the head portion 200 includes a distal end portion 210. The distal end portion 210 includes a geometry that is keyed to a proximal region 310 of the inner cannulation 308 of the outer shaft portion 300. The proximal region 310 extends at least partially from the proximal end 302 toward the inner distal end 304. As seen in FIG. 12, the inner channel 202 extends through the distal end portion 210. The distal end portion 210 includes a hexagonal cross-section as shown in FIG. 10. The hexagonal cross-section is configured to oppose rotation of the distal end portion 210 of the head within the inner cannulation 308 of the outer shaft portion 300 to allow rotation of the head portion 200 to drive rotation of the outer shaft portion 300. Additional alternative cross-sections for the distal end portion 210 are possible. For example, these alternative cross-sections can include other non-rounded cross-sections configured to oppose rotation of the distal end portion 210 within the inner cannulation 308. These additional cross-sections can also include, but are not limited to, a square cross-section, a triangular cross-section, a pentagonal cross-section, etc. Because the proximal region 310 of the outer shaft portion 300 is keyed to the geometry of the distal end portion 210, the proximal region 310 includes a matched cross-sectional profile configured to accommodate the distal end portion 210.

Figure 13:
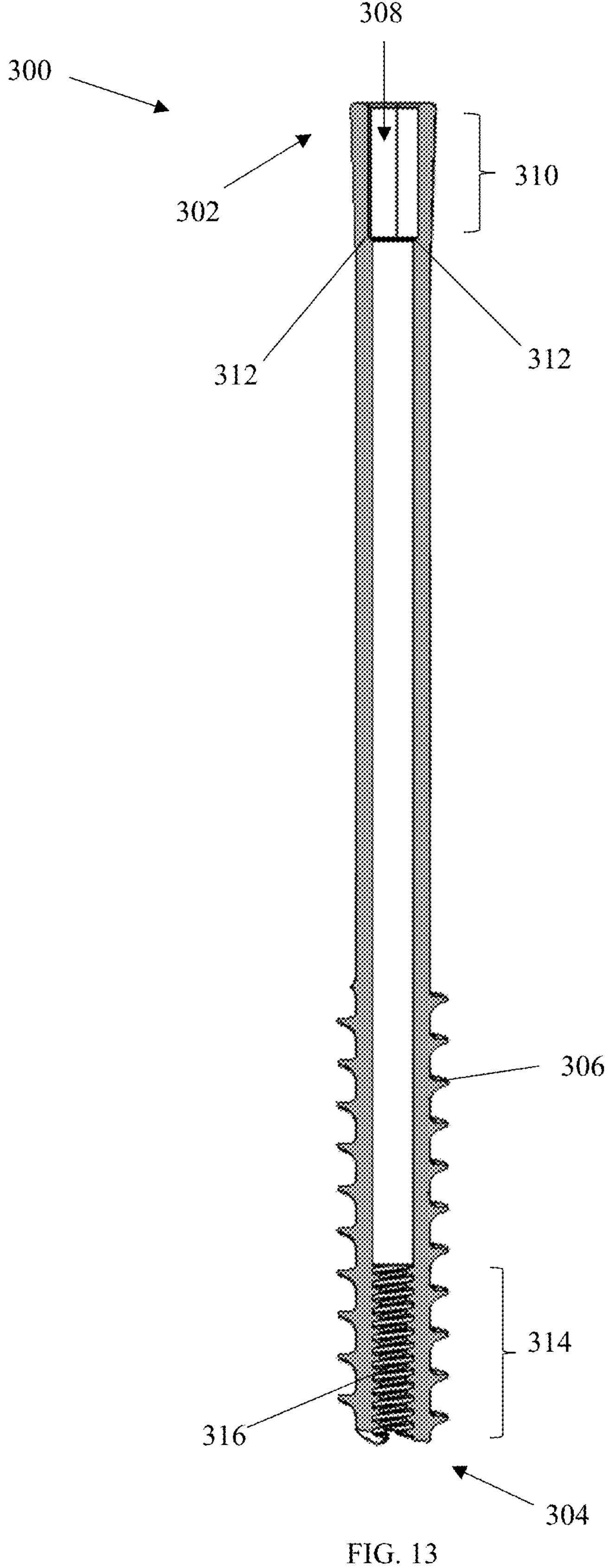
FIG. 13 is a cross-sectional view of the outer shaft portion of the orthopedic taken along the line A-A in FIG. 2 with the head portion and inner shaft portion of the compression device of FIG. 1 removed.
Figure 16:
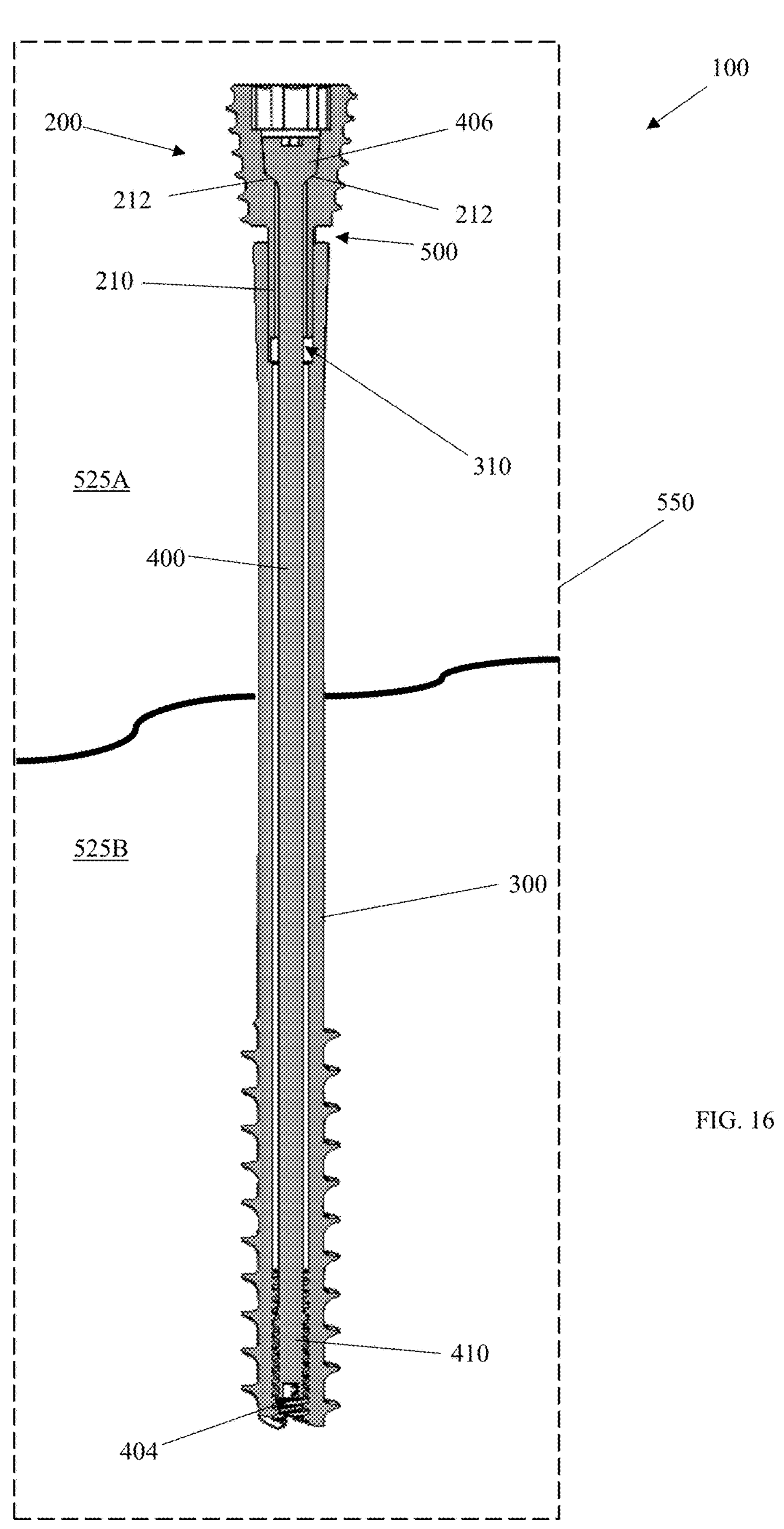
FIG. 16 is a cross-sectional view of the orthopedic compression device of FIG. 1 taken along the line A-A in FIG. 2, shown in position across a bone interface and with the inner shaft portion in a tensioned state.

With reference to FIGS. 8 and 12-17, the device is assembled by passing the inner shaft portion 400 through the inner channel 202 of the head portion 200 until the stop 406 engages a stop surface 212 formed within the inner channel 202 (see FIG. 12). The distal end portion 210 is fed into the proximal region 310 of the outer shaft portion 300 with which it has a keyed geometry until the distal end 205 engages with a stop surface 312 located at the end of the proximal region 310 closest to the inner distal end 304 and/or a shoulder surface 214 of the head portion 200 contacts the proximal end 302 of the outer shaft portion 300. The distal end portion 410 is then secured to a distal end portion 314 of the outer shaft portion 300 to secure the distal end portion 210 of the head portion 200 at least partially within the proximal region 310 with which the distal end portion 210 is indexed. As shown in FIGS. 13 and 16, the inner shaft portion 400 is secured inside the inner cannulation 308 of the outer shaft portion 300 by a thread 412 engaging with corresponding a thread 316 of the distal end portion 314 of the outer shaft portion 300. Other ways for coupling the inner shaft portion 400 inside the outer shaft portion 300 are also possible. For example, the inner shaft portion 400 can be fixed with threads or another coupling mechanism anywhere inside the outer shaft portion 300 and not within the distal end portion 314.

Upon installation into the bone 550 of a patient, the head portion is impeded from advancing via occlusion with the first bone portion 525A while the outer shaft portion 300 continues to be driven into the second bone portion 525B, as shown in FIG. 16. Fig. depicts fractured portions of the bone 500, but the device could be used with bone grafts or in other applications where compression is desired or where there is an interface between bone segments.

Figure 17:
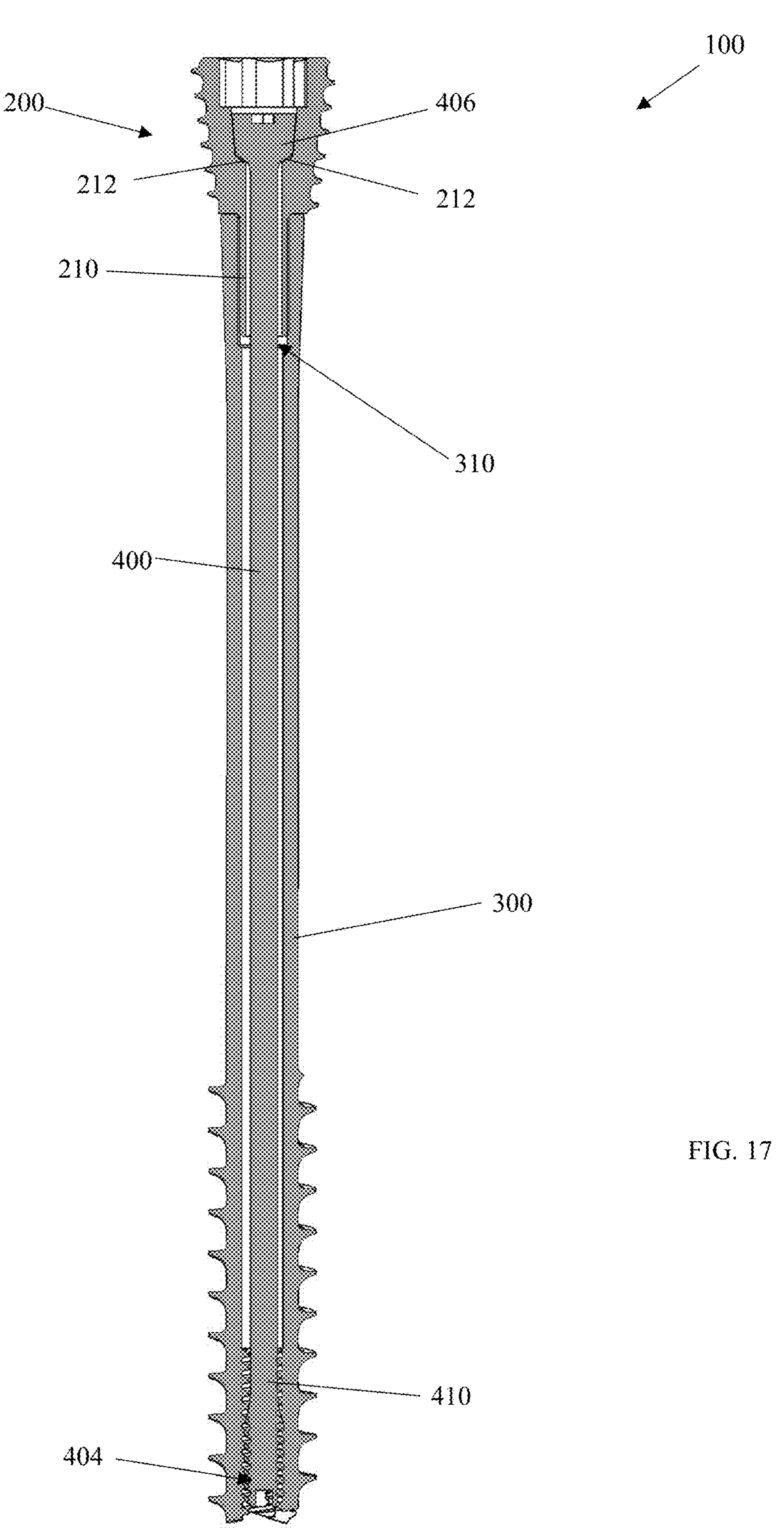
FIG. 17 is a cross-sectional view of the orthopedic compression device of FIG. 1 like that of FIG. 16 but shown with the inner shaft portion in a non-tensioned state.

As seen via comparison with FIG. 17, this causes the distal end portion 210 of the head portion 200 to at least partially retract a distance from the proximal region 310 to form a gap 500 between the shoulder surface 214 and the proximal end 302 after the orthopedic compression device 100 is installed to bridge fractured bone portions 525A and 525B of the bone 550. The inner shaft portion 400 then elongates and is placed into tension upon separation of the proximal end 204 of the head portion 200 and the inner distal end 304 of the outer shaft portion 300, as is facilitated by the superelastic properties of the material used to form the inner shaft portion 400. As shown in FIG. 17, when the orthopedic compression device 100 is initially formed by joining together the head portion 200, the outer shaft portion 300, and the inner shaft portion 400, the gap 500 is not present between the head portion 200 and the outer shaft portion 300, and the inner shaft portion 400 is not elongated.

The device may be sized such that the gap 500 may extend any suitable length. In some cases, the device may be configured to accommodate a gap of as much as 5 mm initially in orthopedic use. After some resorption of the bone 550 and healing of the patient, the gap 500 can decrease, for example, to approximately 3-4 mm. The device may be otherwise sized and configured depending on the intended use.

Figure 18:
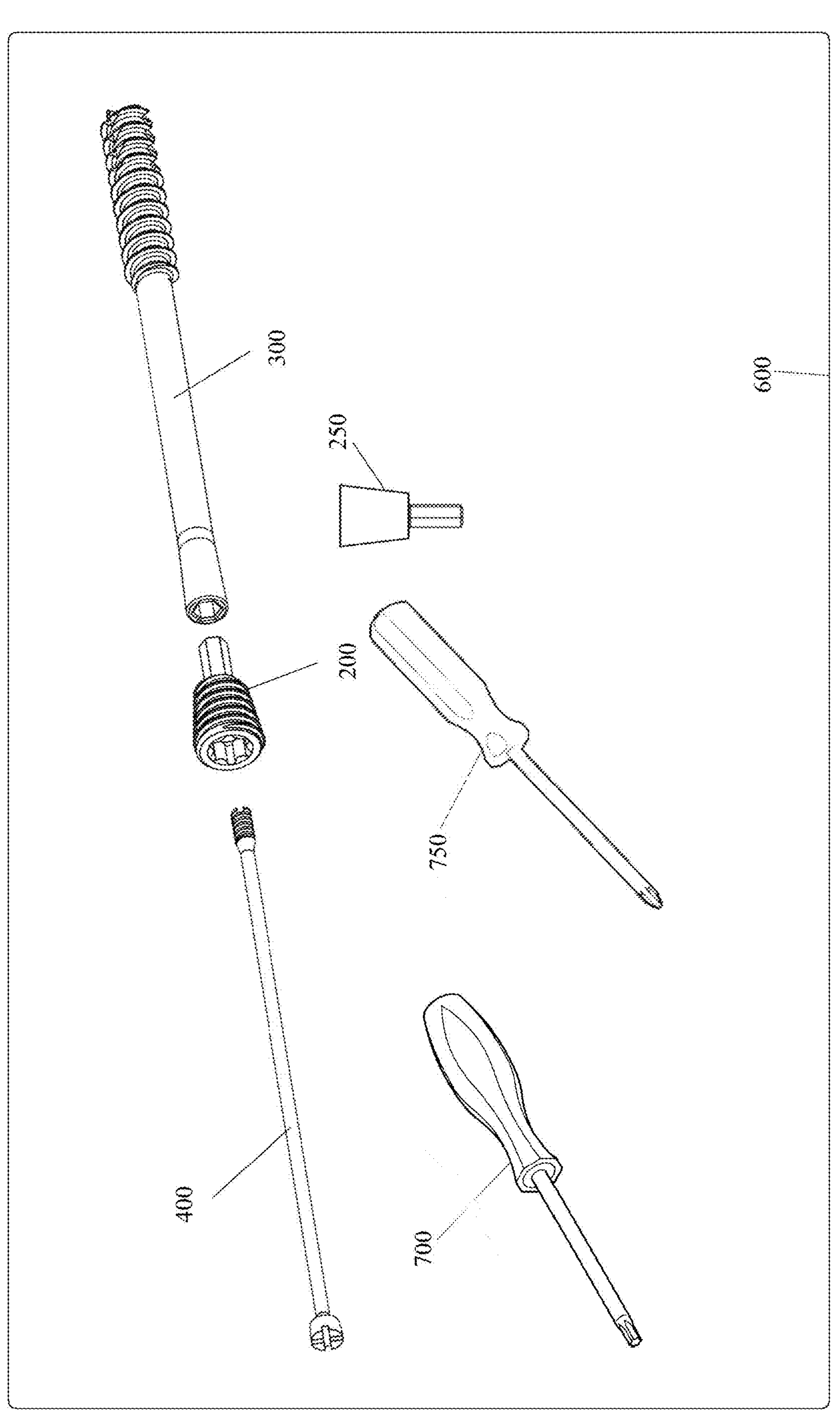
FIG. 18 is a schematic representation of a kit in accordance with the present disclosure. The drivers shown in the kit are not to scale.

With reference now to FIG. 18, a kit includes a container 600 having the head portion 200, an optional second head portion 250, the outer shaft portion 300, the inner shaft portion 400, the first driver 700, and a second driver 750. The second head portion 250 includes an unthreaded bone-engaging external flared surface in place of the thread 208. Other embodiments for the kit 600 are also possible. For example, the kit can include the orthopedic compression device 100 in a fully formed configuration with the head portion 200 or the second head portion 250 joined to the outer shaft portion 300 and the inner shaft portion 400. In these embodiments, the corresponding second driver 750 could be omitted. In other embodiments, different versions of the outer shaft portion 300 can be included in the kit, such as versions of the outer shaft portion 300 with a different thread pitch or number of threads used for joining the orthopedic compression device 100 into different section of the patient.

The embodiments described herein are also directed to a method for assembling the orthopedic compression device 100. The method includes providing the outer shaft portion 300, the inner shaft portion 400, and the head portion 200 and/or the second head 250. Then, the method includes passing the distal end 404 of the inner shaft portion 400 through inner channel 202 of the head portion 200 (or the similar channel in the second head 250) until the stop 406 engages with the stop surface 212 formed within the inner channel 202. The method also includes introducing the distal end 404 of the inner shaft portion 400 into the inner cannulation 308 of the outer shaft portion 300 and securing and/or coupling the distal end 404 inside the inner cannulation 308. The method can also include securing the distal end 404 of the inner shaft portion 400 inside the inner cannulation 308 by engaging the driver 750 with the driver interface 408 included on the proximal end 402 of the inner shaft portion 400 and rotating the driver until the distal end of the second shaft is securely coupled inside the inner cannulation 308 of the outer shaft portion 300. Further, in some embodiments, the surgeon might wish to increase the compressive load applied between bone segments such as the bone portions 525A and 525B of the bone 550 after the orthopedic compression device 100 is initially secured within the patient. Such an increase in compressive force can be accomplished by further advancing the inner shaft portion 400 within the outer shaft portion 300 using, for example, a second driver 750.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. An orthopedic compression device comprising:

an outer shaft portion having a threaded outer distal end and having an inner cannulation extending from an opening in a proximal end towards an inner distal end, the inner cannulation having a proximal region;

a head portion, the head portion having a distal end portion with a geometry matched to the proximal region of the cannulation of the outer shaft portion and configured to allow rotation of the head portion to drive rotation of the outer shaft portion, the head portion including an inner channel, wherein the head portion includes a threaded external surface; and an inner shaft portion, the inner shaft portion formed from a superelastic material and having a stop at a proximal end thereof, the stop engaging a stop surface formed within the head portion, the inner shaft portion extending through the inner channel and coupled to the outer shaft portion;

wherein the inner shaft portion elongates and is placed into tension upon separation of the head portion and outer shaft portion to thereby cause a compressive force between said head portion and said outer shaft portion upon said separation, wherein a proximal end of the head portion includes a first driver interface configured to receive a corresponding first driver used to rotate said head portion and to cause driven rotation of the outer shaft portion;

wherein the inner shaft portion includes a thread disposed on a distal end thereof, the thread engaging a thread on the inner distal end of the outer shaft portion to cause coupling of the inner shaft portion and the outer shaft portion, and wherein the inner shaft portion includes a second driver interface that is accessible via a distal opening in the inner cannulation of the outer shaft portion.

2. The orthopedic compression device of claim 1, wherein the first driver interface comprises a star driver slot.

3. The orthopedic compression device of claim 1, wherein threading on the threaded external surface of the head portion has a different thread pitch from a pitch of threading on the threaded outer distal end of the outer shaft portion.

4. A medical procedure kit comprising, within a container, the orthopedic compression device of claim 1, and a first driver, the first driver corresponding to said first driver interface.

5. A medical procedure kit comprising, within a container, the orthopedic compression device of claim 1, and a second head portion, the second head portion including an unthreaded bone-engaging external surface.

6. A method comprising providing the orthopedic compression device of claim 1, driving said threaded outer distal end of said outer shaft portion into bone across a bone interface a sufficient distance to cause separation of said head portion and said outer shaft portion, whereby said inner shaft portion elongates and is placed under tension to cause a compressive force across said bone interface.

7. The method of claim 6, wherein threading on the threaded external surface of the head portion has a different thread pitch from a pitch of threading on the threaded outer distal end of the outer shaft portion.

8. A method for assembling an orthopedic compression device, the method comprising:

providing an outer shaft portion having a threaded outer distal end and having an inner cannulation extending from an opening in a proximal end towards an inner distal end, the inner cannulation having a proximal region; a head portion, the head portion having a distal end portion with a geometry matched to the proximal region of the cannulation of the outer shaft portion and configured to allow rotation of the head portion to drive rotation of the outer shaft portion, the head portion including a first driver interface, an inner channel, an inner stop surface, and a threaded external surface; and an inner shaft portion, the inner shaft portion formed from a superelastic material and having a stop at a proximal end thereof;

passing a distal end of the inner shaft portion through the inner channel of the head until the stop of the inner shaft portion engages said stop surface;

introducing the distal end of the inner shaft portion into the inner cannulation of the outer shaft portion through said opening in said proximal end; and coupling the inner shaft portion to the outer shaft portion, the distal end portion of the head portion at least partially disposed within the proximal region of the inner cannulation of the outer shaft portion, wherein coupling the inner shaft portion to the outer shaft portion includes inserting a driver through a distal opening in the inner cannulation of the outer shaft portion, engaging said driver with a second driver interface disposed at the distal end of the inner shaft portion, and rotating the driver.

9. The method of claim 8, wherein the first driver interface comprises a star driver slot and the second driver interface comprises a Phillips driver slot.

10. The method of claim 8, wherein the inner shaft portion includes a thread disposed on a distal end thereof, the thread engaging with a thread on the inner distal end of the outer shaft portion to cause coupling of the inner shaft portion and the outer shaft portion.

11. The method of claim 8, wherein threading on the threaded external surface of the head portion has a different thread pitch from a pitch of threading on the threaded outer distal end of the outer shaft portion.

12. The method of claim 8, wherein a proximal end of the head portion includes the first driver interface configured to receive a corresponding first driver used to rotate said head portion and to cause driven rotation of the outer shaft portion.

* * * * *